(12) United States Patent
Viot

(10) Patent No.: US 7,153,521 B2
(45) Date of Patent: Dec. 26, 2006

(54) COMPOSITION COMPRISING A LIQUID ABSORBED ON A SUPPORT BASED ON PRECIPITATED SILICA

(75) Inventor: Jean-François Viot, Irigny (FR)

(73) Assignee: Rhodia Chimie, Aubervilliers (FR)

( * ) Notice: Subject to any disclaimer, the term of this patent is extended or adjusted under 35 U.S.C. 154(b) by 417 days.

(21) Appl. No.: 10/265,038

(22) Filed: Oct. 4, 2002

(65) Prior Publication Data

US 2003/0035823 A1 Feb. 20, 2003

Related U.S. Application Data

(63) Continuation of application No. 09/424,638, filed on Nov. 29, 1999, now abandoned.

(30) Foreign Application Priority Data

Mar. 30, 1998 (FR) .................................. 98 03909

(51) Int. Cl.
| | |
|---|---|
| A61K 9/14 | (2006.01) |
| A61K 9/16 | (2006.01) |
| A23K 1/17 | (2006.01) |
| A23K 1/165 | (2006.01) |

(52) U.S. Cl. ........................ 424/442; 424/489; 424/490
(58) Field of Classification Search ................ 424/442, 424/489

See application file for complete search history.

(56) References Cited

U.S. PATENT DOCUMENTS

| 4,717,561 A | * | 1/1988 | Krivak et al. ................ 423/335 |
| 5,635,214 A | * | 6/1997 | Ponchon et al. ............ 424/489 |
| 5,882,617 A | * | 3/1999 | Chevallier et al. .......... 423/339 |
| 5,906,843 A | | 5/1999 | Dew et al. ..................... 426/2 |

* cited by examiner

*Primary Examiner*—Carlos A Azpuru
*Assistant Examiner*—David Vanik

(57) ABSTRACT

The invention concerns a conditioned composition comprising at least a liquid absorbed on a support containing a precipitated silica, said silica being in the form of substantially spherical pellets and having: an average pellet size greater than 150 μm; a filling density in compacted state (DRT) less than 0.29; an oversize rate for a sieve with aperture size of 75 μm of at least 88% wt. %; a porous volume ($V_{d1}$), consisting of pores with diameter less than 1 μm, greater than 2.0 cm3/g. The invention also concerns the use of said silica as a support for liquid.

13 Claims, No Drawings

US 7,153,521 B2

COMPOSITION COMPRISING A LIQUID ABSORBED ON A SUPPORT BASED ON PRECIPITATED SILICA

This application is a continuation of U.S. application Ser. No. 09/424,638, filed on Nov. 29, 1999. The application claims priority to FR 98/03909 Mar. 30, 1998.

The present invention concerns a composition comprising a liquid, in particular a liquid supplement for animal feed, absorbed on a support based on a particular precipitated silica.

It also relates to the use of this silica as a support for liquid.

It is known to condition liquids, in particular animal feed additives, on solid supports, in particular on a silica support. The aim of this conditioning is generally to convert a liquid which is not, or not readily handleable into a fluid powder that can be stored with ease, for example in bags, and can be handled more straightforwardly, thus being readily dispersible and easy to mix with other divided solid constituents.

In the explanation which follows, the term conditioned composition will be used to refer to the composition thus obtained, that is to say a liquid absorbed on a silica support.

This conditioned composition is to be readily handleable, which implies a high degree of fluidity and little dust formation. It is also to contain a fairly large proportion of active material (liquid) and to have a fairly high density. These various requirements are sometimes contradictory, and are often not fulfilled by the silica supports of the prior art.

The principal object of the invention is thus to provide a novel form of conditioned composition which furthermore advantageously has both a high degree of fluidity, produces little or no dust and preferably has a fairly high density.

To this end, the Applicant Company has found it particularly satisfactory to use a precipitated silica which, amongst other things, has a highly specific morphology, in the case in point being in the form of substantially spherical beads, and a relatively high average particle size, as a support for liquids, for the chloride salt of choline, for example.

In the following explanation, the average particle size is measured according to the standard NF X 11507 (December 1970) by dry screening and determining the diameter corresponding to a 50% cumulative residue.

The packed filling density (PFD) is determined according to the standard NF T 30-042.

The DOP oil absorption value is measured according to the standard NF T 30-022 (March 1953) using dioctylphthalate.

The pore volumes which are given are measured by mercury porosymmetry; each sample may be prepared as follows: each sample is predried for 2 hours in an oven at 200° C., then placed in a test container within 5 minutes after removal from the oven and degassed under vacuum, for example using a rotary valve pump; the pore diameters are calculated using WASHBURN's relationship with a contact angle theta equal to 140° and a surface tension gamma equal to 484 dynes/cm (MICROMERITICS 9300 porosimeter).

The BET specific surface is determined according to the BRUNAUER-EMMET-TELLER method described in "The journal of the American Chemical Society", Vol. 60, page 309, February 1938 and corresponding to the standard NF T 45007 (November 1987).

The CTAB specific surface is the external surface area determined according to the standard NF T 45007 (November 1987) (5.12).

The flow time $t_f$ of the conditioned compositions, which illustrates their fluidity, is measured by passing 50 grams of product through a glass hopper with a calibrated orifice: cylinder diameter: 50 mm; cylinder height: 64 mm; cone angle: 53°; passage diameter at cone base: 12 mm. According to this method, the hopper, which is closed at its base, is filled using 50 grams of product; then its base is opened and the transit time, referred to as the flow time $t_f$ of the product, after all of the said 50 grams have flowed through is noted.

The composition according to the invention comprises at least one liquid absorbed on a support containing a precipitated silica, the said precipitated silica being in the form of substantially spherical beads, and having:
  an average bead size in excess of 150 µm,
  a packed filling density (PFD) lower than 0.29,
  a 75 µm screen oversize of at least 88% by weight,
  a pore volume ($V_{d1}$), made up of pores having a diameter smaller than 1 µm, in excess of 2.0 cm$^3$/g.

The precipitated silica used in the conditioned composition according to the invention is thus in a highly specific form, in the case in point in the form of substantially spherical beads.

The average size of the said beads is in excess of 150 µm, and advantageously equal to at least 200 µm; in general, it is at most 320 µm, preferably at most 300 µm; it may be between 200 and 290 µm, in particular between 210 and 285 µm, for example between 215 and 280 µm. This size may, in particular, be between 260 and 280 µm.

The packed filling density (PFD) of this precipitated silica is lower than 0.29. It is preferably relatively high and then strictly between 0.24 and 0.29, in particular between 0.25 and 0.28.

This silica has a 75 µm screen oversize of at least 88% by weight. This means that at least 88% by weight, of the particles of this silica are retained by a screen whose mesh size is 75 µm.

This silica thus has a low proportion by weight of rather fine particles.

Preferably, its 75 µm screen oversize is at least 90% by weight, in particular at least 92% by weight, or even at least 93% by weight, and it can be lower that 94% by weight.

It is, for example, at least 90% by weight and lower than 96% by weight, in particular than 94% by weight.

The precipitated silica used in the conditioned composition according to the invention therefore produces little dust.

The said silica has a pore volume ($V_{d1}$), made up of pores having a diameter smaller than 1 µm, in excess of 2.0 cm$^3$/g, in particular at least 2.1 cm$^3$/g, for example at least 2.2 cm$^3$/g.

It customarily has an oil absorption value (DOP) of at least 270 ml/100 g, preferably at least 275 ml/100 g, in particular in excess of 280 ml/100 g. It may thus be between 275 and 320 ml/100 g, for example between 280 and 310 ml/100 g in particular between 280 and 295 ml/100 g.

Its BET specific surface is generally between 140 and 240 m$^2$/g, in particular between 140 and 200 m$^2$/g. It is for example between 150 and 190 m$^2$/g. It may in particular be between 160 and 170 m$^2$/g.

Its CTAB specific surface may be between 140 and 230 m$^2$/g, in particular between 140 and 190 m$^2$/g. It is for example between 150 and 180 m$^2$/g, in particular between 150 and 165 m$^2$/g It generally has a low moisture content; its moisture content (loss on drying at 105° C. for 2 hours) is preferably less than 6% by weight, for example less than 5% by weight.

Advantageously, the silica employed in the composition according to the invention results from the use of a nozzle atomizer to dry a suspension of silica obtained by precipitation. Preferably, the said silica suspension to be dried has a solids content of between 18.0 and 20.5% by weight, in particular between 18.5 and 20.0% by weight, especially between 19.0 and 20.0% by weight.

This silica may be prepared according to a process of the type comprising the reaction of a silicate with an acidifying agent, by means of which a suspension of precipitated silica is obtained, following which this suspension is separated and dried using a nozzle atomizer, the precipitation being carried out in the following way:

1) an initial stock solution is formed, containing at least some of the total amount of silicate employed in the reaction and, in general, at least one electrolyte, the silicate concentration (expressed as $SiO_2$) in the said initial stock solution being less than 100 g/l, in particular 90 g/l, and the electrolyte concentration (for example sodium sulphate) in the said initial stock solution being less than 17 g/l, for example less than 14 g/l, 2) the acidifying agent is added to the said stock solution until a pH value of at least about 7, generally between about 7 and 8, is obtained for the reaction medium, 3) acidifying agent is added to the reaction medium, where appropriate together with the remaining amount of the silicate at the same time, the suspension to be dried having a solids content of between 18.0 and 20.5% by weight, in particular of between 18.5 and 20.0% by weight.

It should be noted in general that the process in question is a process for synthesizing silica by precipitation, that is to say an acidifying agent is reacted with a silicate under specific conditions.

The choice of the acidifying agent and of the silicate is made in a manner which is well known per se.

It may be recalled that the acidifying agent generally used is a strong inorganic acid such as sulphuric acid, nitric acid or hydrochloric acid, or an organic acid such as acetic acid, formic acid or carbonic acid.

The acidifying agent may be dilute or concentrated; its normality may be between 0.4 and 8 N, for example between 0.6 and 1.5 N.

In particular, in the case when the acidifying agent is sulphuric acid, its concentration may be between 40 and 180 g/l, for example between 60 and 130 g/l.

Any common form of silicate, such as metasilicates, disilicates and advantageously an alkali metal silicate, in particular sodium or potassium silicate, may moreover be used as the silicate.

The silicate may have a concentration, expressed as silica, of between 40 and 330 g/l, in particular between 60 and 300 g/l, for example between 60 and 250 g/l.

In general, sulphuric acid is used as the acidifying agent and sodium silicate is used as the silicate.

In the case when sodium silicate is used, it generally has an $SiO_2/Na_2O$ weight ratio of between 2 and 4, for example between 3.0 and 3.7.

The initial stock solution generally comprises an electrolyte. The term electrolyte is intended to be understood here in its normal meaning, that is to say it indicates any ionic or molecular substance which, when it is in solution, decomposes or dissociates to form ions or charged particles. Examples of electrolytes which may be mentioned include a salt of the group consisting of the salts of the alkali and alkaline-earth metals, in particular the salt of the metal of the starting silicate and of the acidifying agent, for example sodium chloride in the case of reacting a sodium sulfate with hydrochloric acid, or preferably sodium silicate in the case of reacting a sodium silicate with sulphuric acid.

In the (preferred) case of a starting stock solution comprising only some of the total amount of the silicate employed in the reaction, simultaneous addition of acidifying agent and the remaining amount of silicate is carried out in step (3).

This simultaneous addition is preferably carried out in such a way that the pH is continuously equal (to within +/−0.2) to the value reached at the end of step (2).

In general, in a subsequent step, an additional amount of acidifying agent is added to the reaction medium, preferably until the pH obtained for the reaction medium has a value of between 3 and 6.5, in particular between 4 and 6.5.

It may then be advantageous, after this addition of an extra amount of acidifying agent, to mature the reaction medium, it being possible for this maturation to last, for example, from 2 to 60 minutes, in particular from 3 to 20 minutes.

In the case of a starting stock solution containing the total amount of the silicate employed in the reaction, acidifying agent is preferably added in step (3) until a pH for the reaction medium is obtained with a value of between 3 and 6.5, in particular between 4 and 6.5.

It may then be advantageous, after this step (3), to mature the reaction medium, it being possible for this maturation to last, for example, from 2 to 60 minutes, in particular from 3 to 20 minutes.

The temperature of the reaction medium is generally between 70 and 98° C.

According to a variant of the process, the reaction is carried out at a constant temperature, preferably of between 80 and 95° C.

According to another (preferred) variant of the process, the temperature at the end of the reaction is higher than the temperature at the start of the reaction: thus, the temperature at the start of the reaction is preferably maintained at between 70 and 95° C., then the temperature is increased, preferably to a value of between 80 and 98° C., at which value it is maintained until the end of the reaction.

At the end of the steps which have just been described, a silica broth is obtained which is then separated (liquid/solid separation).

In general, the said separation comprises filtration and washing using a filter equipped with a compacting means.

This filter may be a belt filter equipped with a roller which performs the compaction.

Nevertheless, this filter is preferably a filter press, and the separation then generally comprises filtration, washing then compacting with the aid of the said filter.

The suspension of precipitated silica recovered in this way (filter cake) is then spray-dried using a nozzle atomizer.

It is highly advantageous for this suspension to have a solids content between 18.0 and 20.5% by weight, in particular between 18.5 and 20.0% by weight, for example between 19.0 and 20.0% by weight, immediately before it has been dried.

It should be noted that the filter cake is not always in a form suitable for atomization, in particular because it has high viscosity. In a manner which is known per se, the cake is then subjected to a crumbling operation. This operation may be carried out by passing the cake through a mill of the colloidal or ball type. The crumbling is generally carried out in the presence of an aluminium compound, in particular sodium aluminate. The crumbling operation makes it possible, in particular, to lower the viscosity of the suspension which is subsequently to be dried.

The Applicant Company has found that the precipitated silica as defined above, therefore having a highly specific morphology, in the case in point being in the form of substantially spherical and dense beads, and a relatively large average-particle size, had a high degree of fluidity and produced little dust, and was particularly well suited to the conditioning of liquids.

Examples of liquids which may be mentioned include, in particular, organic liquids such as organic acids, surfactants, for example used in detergents, either of the ionic type such as sulphonates or of the non-ionic type such as alcohols, organic additives for rubber, and pesticides Preservatives (phosphoric acid, propionic acid in particular), flavourings and colorants may be used as the liquids.

The Applicant Company has observed that the precipitated silica described above was particularly suited to the conditioning of nutritional supplements in liquid form, in particular for animal feed.

The liquid contained in the conditioned composition according to the invention is thus preferably a liquid supplement for animal feed. Mention may be made in particular of vitamins such as vitamin E, choline and, preferably, its chloride salt.

The operation of absorbing the liquid on the support based on the said precipitated silica may be carried out in the conventional way, in particular by spraying the liquid onto the silica in a mixer.

Although the amount of liquid absorbed generally depends on the intended application, the composition according to the invention customarily has, in particular in the case of the chloride salt of choline, a liquid content of at least 60% by weight, in particular between 60 and 75% by weight, especially between 60 and 70% by weight (relative to the total weight of the composition); it may for example be between 63 and 68% by weight, especially between 64 and 67% by weight.

Lower liquid contents may be used, in particular in the case of vitamin E.

Owing to the presence of the precipitated silica having the abovementioned characteristics, the conditioned composition according to the invention advantageously produces, especially in the case of the chloride salt of choline and in particular for a content of the chloride salt of choline of between 63 and 68% by weight, preferably 64 and 67% by weight, little or no dust and has a very high degree of fluidity, these properties being combined, in general, with a high density.

The conditioned composition according to the invention, in particular in the case of the chloride salt of choline, preferably has a flow time $t_f$ (measured for 50 grams of product and for a passage diameter of 12 mm) of less than 11 seconds, in particular of at most 10 seconds, especially of less than 7 seconds, which evinces its very high degree of fluidity.

Furthermore, the conditioned composition according to the invention, in particular in the case of the chloride salt of choline, customarily has a packed filling density (PFD) of at least 0.68, for example of at least 0.70, especially of at least 0.72.

Finally, in general, the said precipitated silica provides this composition, in particular in the case of the chloride salt of choline, with a 75 µm screen oversize of at least 95% by weight, in particular of at least 96% by weight. This ratio, in particular in the case of the chloride salt of choline, is preferably at least 97% by weight, for example at least 98% by weight. This composition thus customarily has a very low proportion by weight of fine particles. It therefore produces little or no dust.

The invention also relates to the use of the precipitated silica described above as a support for liquid, such as for example one of the liquids mentioned above.

The following example illustrates the invention, but without limiting its scope.

EXAMPLE

1) The following ingredients:
345 liters of water
7.5 kg of $Na_2SO_4$
588 liters of aqueous sodium silicate having an $SiO_2/Na_2O$ weight ratio equal to 3.5 and a density at 20° C. equal to 1.133 are introduced into a stainless-steel reactor fitted with an impeller stirring system and a jacket heating system.

The silicate concentration expressed as $SiO_2$, in the initial stock solution is thus 85 g/l. The mixture is then heated to a temperature of 79° C. while continuing to stir it. 387 liters of dilute sulphuric acid, with a density at 20° C. equal to 1.050, are then introduced therein until a pH equal to 8.0 is obtained in the reaction medium (value measured at the temperature of the medium). The reaction temperature is 79° C. for the first 25 minutes; it is then increased from 79 to 86° C. in 15 minutes, then maintained at 86° C. until the end of the reaction.

82 liters of aqueous sodium silicate, of the type described above, and 134 liters of sulphuric acid, also of the type described above, are then jointly introduced into the reaction medium (that is to say when the pH of the reaction medium has reached a value of 8.0), this simultaneous introduction of acid and of silicate being carried out in such a way that the pH of the reaction medium is continuously equal to 8.0±0.1 throughout the introduction period. After all of the silicate has been introduced, introduction of the dilute acid is continued for 9 minutes so as to bring the pH of the reaction medium to a value equal to 5.2. After this introduction of acid, stirring of the reaction broth which is obtained is continued for 5 minutes.

The total reaction time is 118 minutes.

A precipitated silica broth or suspension is thus obtained, which is then filtered and washed using a filter press with vertical plates (the said plates being equipped with a deformable diaphragm allowing the filter cake to be compressed by introducing pressurized air), at a pressure of 4.5 bar and for the time needed to obtain a silica cake whose loss on ignition is equal to 80.5% (therefore a solids content of 19.5% by weight).

The cake obtained is then fluidized by mechanical and chemical action (addition of an amount of sodium aluminate corresponding to an $Al/SiO_2$ weight ratio of 3000 ppm); during this operation, water is added so as to obtain a broth having a loss on ignition equal to 81.5% (and therefore a solids content of 18.5% by weight). After this crumbling operation, the resulting broth, with a pH equal to 6.4, is dried using a nozzle atomizer.

The precipitated silica P1 which is obtained is in the form of substantially spherical beads and has the following additional characteristics:

| | |
|---|---|
| average particle size | 260 µm |
| PFD | 0.28 |
| 75 µm screen oversize | 93.0% |
| DOP oil absorption value | 290 ml/100 g |
| pore volume ($V_{d1}$) made up of pores with d < 1 µm | 2.1 $cm^3/g$ |

2) The chloride salt of choline is placed on a support formed by the silica Pi prepared in 1).

The chloride salt of choline is placed on the support in a 7-liter V mixer rotating at 20 rpm, with an inner shaft rotating at 1900 rpm, fitted with plates through which the chloride salt of choline is sprayed, and on which emitter blades are fixed.

All of the silica P1 is introduced into the mixer, then the chloride salt of choline is sprayed (at a temperature of 70° C. and at a rate of 100 ml/min) onto this silica. Mixing is carried out for 15 minutes, then homogenization is carried out for a further 2 minutes.

The conditioned composition then obtained contains 34% by weight of precipitated silica Pi and 66% by weight of chloride salt of choline, and has the following additional characteristics:

| | |
|---|---|
| flow time $t_f$ | 6.5 seconds |
| PFD | 0.70 |
| 75 μm screen oversize | >95% |

This conditioned composition based on a precipitated silica support, in the form of substantially spherical beads, thus has a very high degree of fluidity (which is illustrated in particular by a short flow time $t_f$) and produces no dust (which is illustrated in particular by a high 75 μm screen oversize), while having a rather high density.

The invention claimed is:

1. A conditioned composition comprising at least one liquid absorbed on a support containing a precipitated silica, said silica being in the form of substantially spherical beads and having:
   a DOP oil absorption value of at least 270 ml/100 g,
   an average bead size of between 200 and 320 μm,
   a packed filling density of strictly between 0.24 and 0.29,
   a 75 μm screen oversize of at least 88% by weight, and
   a pore volume ($V_{d1}$), made up of pores having a diameter smaller than 1 μm, in excess of 2.0 cm$^3$/g,
   said composition having a liquid content of at least 60% by weight.

2. The composition according to claim 1, wherein said silica has an average bead size of between 200 and 290 μm.

3. The composition according to claim 1, wherein said silica has a 75 μm screen oversize of at least 90% by weight.

4. The composition according to claim 1, wherein said silica further has a DOP oil absorption value of between 275 and 320 ml/100 g.

5. The composition according to claim 1, wherein said silica has a pore volume ($V_{d1}$) made up of pores having a diameter smaller than 1 μm, in excess of at least 2.1 cm$^3$/g.

6. The composition according to claim 1, wherein said silica is made by the process of drying a suspension of silica obtained by precipitation with a nozzle atomiser.

7. The composition according to claim 6, wherein, before drying, said silica suspension has a solids content of between 18.0 and 20.5% by weight.

8. The composition according to claim 7, wherein, before drying, said silica suspension has a solids content of between 18.5 and 20.0% by weight.

9. The composition according to claim 1, wherein said composition has a liquid content of between 60 and 75% by weight.

10. The composition according to claim 1, wherein said liquid is a preservative, a flavouring, a colorant or a liquid supplement for animal feed.

11. The composition according to claim 1, wherein said liquid is the chloride salt of choline.

12. The composition according to claim 1, wherein said composition further has a flow time $t_f$ of less than 11 seconds for 50 grams and for a passage diameter of 12 mm.

13. The composition according to claim 12, wherein said flow time $t_f$ is less than 7 seconds.

* * * * *